United States Patent [19]
Imaino et al.

[11] Patent Number: 5,945,685
[45] Date of Patent: Aug. 31, 1999

[54] GLASS SUBSTRATE INSPECTION TOOL HAVING A TELECENTRIC LENS ASSEMBLY

[75] Inventors: Wayne Isami Imaino; Anthony Juliana, Jr.; Milton Russell Latta; Charles Cheng-Hsing Lee; Wai Cheung Leung, all of San Jose; Hal Jervis Rosen, Los Gatos, all of Calif.

[73] Assignee: International Business Machines Corporation, Armonk, N.Y.

[21] Appl. No.: 08/974,272

[22] Filed: Nov. 19, 1997

[51] Int. Cl.⁶ .................................................... G01N 21/86
[52] U.S. Cl. .................. 250/559.45; 250/225; 356/239.1
[58] Field of Search ............................ 250/559.45, 559.4, 250/225; 356/239.1, 239.2

[56] References Cited

U.S. PATENT DOCUMENTS

4,822,165  4/1989  Schmalfuss et al. ................. 356/239.1
4,873,430  10/1989  Juliana et al. ........................... 250/225

*Primary Examiner*—Que T. Le
*Attorney, Agent, or Firm*—Thomas R. Berthold

[57] ABSTRACT

A glass disk substrate inspection tool uses a polarized laser beam that is directed to the first surface of the disk substrate at Brewster's angle and is then transmitted through the disk substrate to a light detector that generates a signal representative of the intensity of the light received. Because the light polarized parallel to the plane of incidence, i.e., the plane formed by the line of the incident beam and a line perpendicular to the surface of the disk substrate, is completely transmitted, there is no surface reflection at either the first or second surfaces of the disk substrate. The polarized beam is directed by a first rotating scanner to the input of a telecentric lens assembly that provides an output beam parallel to its optical axis as the beam is being scanned. The beam is then directed by a first fixed mirror to strike the first surface of the disk substrate at Brewster's angle as the beam is scanned along a line across the first disk surface. The beam is then transmitted through the substrate to the second surface of the disk substrate to a second fixed mirror that redirects the beam to a second telecentric lens assembly. The light passes through the second telecentric lens assembly in the direction reverse to the direction of passage through the first telecentric lens assembly so that the output beam from the second telecentric lens assembly is directed to its focal point. This focal point coincides with the point of contact of a second rotating scanner synchronized for rotation with the first scanner. The second scanner directs the transmitted beam to the light detector.

18 Claims, 9 Drawing Sheets

GLASS SUBSTRATE INSPECTION TOOL HAVING A TELECENTRIC LENS ASSEMBLY

This application is related to pending application Ser. No. 08/840,351, filed Apr.28, 1997.

FIELD OF THE INVENTION

The invention relates to the field of precision surface analysis for defects. More particularly, the invention relates to laser-based tools for obtaining data on surface features of glass substrates by optical means.

BACKGROUND

Magnetic and optical disks require precision surfaces with extremely low defect rates to function properly. A typical magnetic disk comprises a substrate on which multiple layers of various materials are deposited. For example, a glass or aluminum substrate might be coated with thin films of Cr as an undercoat, a cobalt alloy magnetic layer, and a hydrogenated carbon overcoat. Depending on the stage of the process, these surfaces are not necessarily uniform. For example, a small circular band on the surface of the disk may be textured using a laser to form microscopic bumps. This textured region is intended to provide a low stiction area for the sliders to rest during nonoperating periods. In addition to intentional variations, there may be various types of defects. As the disks progress through the manufacturing process, various tests and inspections are used to detect defective disks so that they may either be reworked or discarded. In addition to visual inspections, a disk may be subjected to glide tests which are sensitive to the flatness of the planar surfaces, as well as magnetic read/write tests. Due to high capacities of magnetic disks, it is typically not practical to magnetically test each bit which can be stored on the disk. Laser surface inspection of the disks, if sufficiently precise, may actually be superior to current magnetic tests in detecting defects. Magnetic defects are usually associated with visible defects, but the visible defects can be detected more efficiently through laser inspection even though the laser spot size is considerably larger than the area in which a bit can be recorded. Thus, laser inspection allows greater test coverage of the disk in a cost-effective manner.

It is also desirable to inspect the disk substrate before any coatings or additional processing steps are added. If surface defects can be detected at this stage, a great savings can be realized by not incurring the costs of additional processing on defective parts.

There are several problems associated with laser-based testing of glass or other light-transmissive disk substrates. First, the glass substrate has a very low reflectivity (approximately 4%), which results in only a small signal amplitude. Secondly, the second surface of the glass substrate also has a very low reflectivity of only approximately 4%, which means that since the transmission through the glass disk is nearly 100%, the second surface produces a reflected beam that interferes with the reflection from the first surface. This results in an unwanted interference fringe pattern in the output.

What is needed is a reliable laser-based surface inspection tool for light-transmissive disk substrates.

SUMMARY OF THE INVENTION

The invention is a glass substrate inspection tool that directs a polarized laser beam to the first surface of the disk substrate at Brewster's angle. The beam then passes through the disk substrate to a light detector that generates a signal representative of the intensity of the light received. Because the light polarized parallel to the plane of incidence, i.e., the plane formed by the line of the incident beam and a line perpendicular to the surface of the disk substrate, is completely transmitted, there is no surface reflection at either the first or second surfaces of the disk substrate. Consequently, no interference fringes are produced.

The polarized beam is directed by a first rotating scanner to the input of a telecentric lens assembly that provides an output beam parallel to its optical axis as the beam is being scanned. The beam is then directed by a first fixed mirror to strike the first surface of the disk substrate at Brewster's angle as the beam is scanned along a line across the first disk surface. The beam is then transmitted through the substrate to the second surface of the disk substrate to a second fixed mirror that redirects the beam to a second telecentric lens assembly. The light passes through the second telecentric lens assembly in the direction reverse to the direction of passage through the first telecentric lens assembly so that the output beam from the second telecentric lens assembly is directed to its focal point. This focal point coincides with the point of contact of a second rotating scanner synchronized for rotation with the first scanner. The second scanner directs the transmitted beam to the light detector. A disk substrate holder moves the substrate in a plane parallel to the surfaces of the substrate so that after the substrate has been scanned along one line, the disk can be moved for scanning along other lines.

In this manner the entire glass disk substrate is inspected for defects, i.e., both surfaces as well as the bulk material between the two surfaces. Thus, a measure of total disk substrate quality includes the defects detected from both surfaces. Because the typical glass disk substrates used for magnetic recording disks are of a very high purity, defects within the bulk material are negligible and do not affect the signal received at the light detector.

For a fuller understanding of the nature and advantages of the present invention, reference should be made to the following detailed description taken together with the accompanying figures.

DETAILED DESCRIPTION OF THE PREFERRED EMBODIMENT

The preferred embodiment of the invention will be described in relation to a laser-based inspection tool for inspecting the planar surfaces of disks for use in disk drives. The inspection may be performed on substrates or finished disks, and is preferably performed on both surfaces of the disk simultaneously. The laser inspection tool (LIT) is general in that it can be used to inspect any sufficiently smooth flat surface at any stage of the process; therefore, it could be used to inspect raw or initial glass or aluminum substrates, aluminum substrates after nickel-phosphorous coating, or finished disks. The LIT uses low-angle reflected light rather than scattered light from the surface to simplify the design, to allow absolute reflectivity measurements if desired, and to aid in the detection of certain types of disk defects such as stains which do not effect the scattering of the light. Stain detection is accomplished through the use of derivative analysis of the reflected light to detect the change in the reflectivity of the surface associated with a disk stain. The system is designed to preserve both the polarization and the wave vector of the reflected light which allows it to be used with minor modifications in a broad range of applications. Using a stable laser, low-noise detectors, and sufficiently high-resolution, analog-to-digital (A/D) converters, it is possible to detect a change in reflectivity of approximately 0.1% using the LIT. Since the surfaces of the disks are extremely sensitive to physical contact, the LIT uses a mechanical lifter which, without clamping or spinning, moves the disk through the laser scan lines to allow the entire surface on each side of the disk to be scanned. Inspection or test systems which require the disks to spin are complex and increase the risk of damage to the disk. The line scanning is performed using a rotating polygon mirror (scanner) which also captures the beam reflected from the disk surface. As the disk is lifted into the scanning area, it passes through a pair of air knives which blow loose particles from both surfaces.

Figure 1:
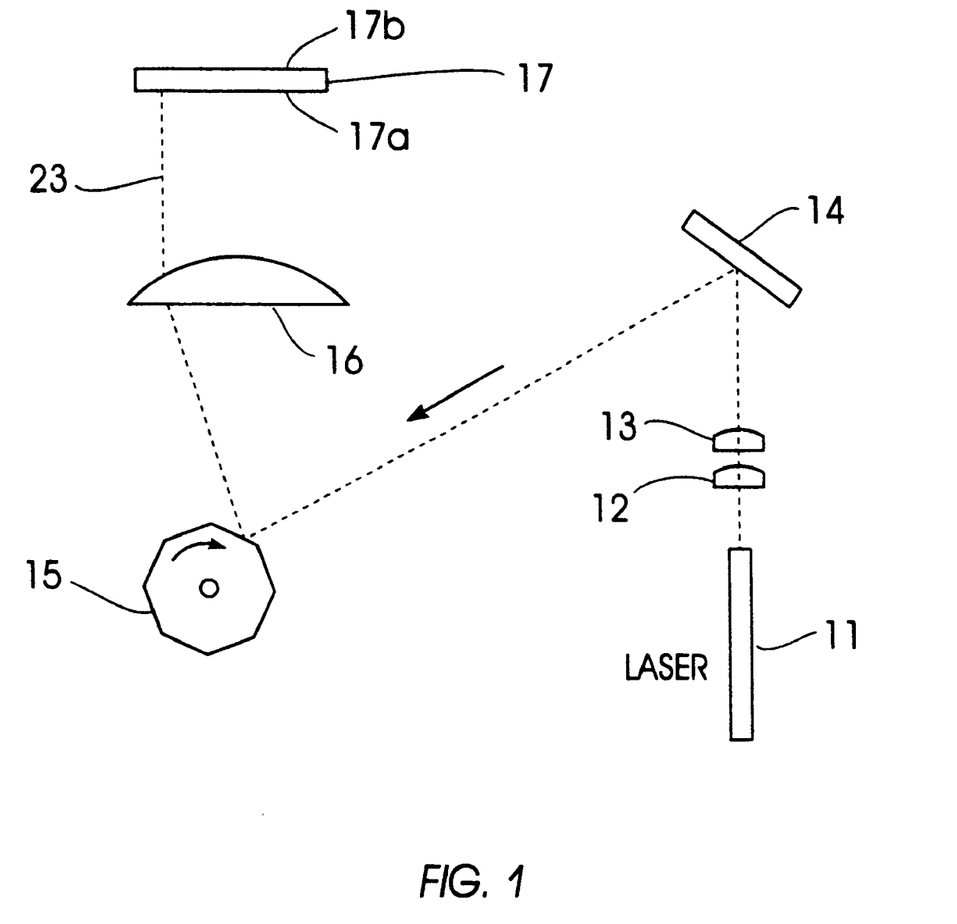
FIG. 1 shows the optical elements in the path from the laser source to the surface to be inspected.

FIG. 1 shows the optical path elements for the optical system of one channel (the A channel) of the LIT from the laser source 11 to the disk 17 and the disk surface to be inspected 17a in a preferred embodiment. The elements in the second channel (the B channel) for inspecting the other surface 17b are identical, but are preferably arranged in a mirror image of the A channel elements and in the same plane. The A and B channels can be assembled on a single baseplate. The choice of low-power laser is not critical, e.g., GaAs, HeNe, etc. are acceptable, but it is preferable that the wavelength be in the visible spectrum for aiding alignment. A few milliwatts of power is sufficient. Since high sensitivity to an absolute amount of reflected light is a goal in the design of the LIT, it is important to select a laser, e.g., HeNe, to minimize noise which might be injected into the system through laser instability. In the preferred embodiment, separate lasers are used for each channel, but it is also possible to use a single laser source with a beam splitter. Lenses 12 and 13 form a telescope (beam expander) which is used to expand the beam 23 (the incident beam). The term "incident beam" (or A beam to specify the A channel) will be used to refer to all segments of the laser beam from generation at the laser 11 along the path to the surface of the disk being inspected (or as will be noted later as an optional calibration mirror). Steering mirror 14 reflects the beam onto the rotating polygon scanner 15 which reflects into the telecentric lens assembly (TLA) 16. The TLA acts to keep the laser beam incident at a constant, nearly perpendicular angle as the beam scans across the disk. The TLA is designed to have a very flat field curvature through the scanning line to keep the spot size sufficiently constant for accurate detection. The figure shows the polygon scanner 15 rotating in a clockwise direction which will cause the incident beam to sweep from left to right across the TLA, and in turn to scan a line across the planar surface of the disk. Each mirrored facet of the polygon corresponds to one scan line across the disk. The choice of a polygon scanner is preferred, but other scanning means, such as a galvonometer mirror, could be used. The polygon scanner 15 is shown as having eight mirrored facets, so as to form a hexagon, but the polygon scanner may have more or fewer facets. The view of FIG. 1 can be considered to be a top view which shows only the top edge of the disk or other item having the planar surface to be inspected. The TLA should have a usable optical scan line which is at least equal to, and preferably slightly longer than, the desired scan length. A laser spot size on the disk of approximately 50 microns in diameter provides sufficient resolution for detecting defects in current disks. Smaller spot size can be used to increase the maximum resolution of the system if desired by altering the focal lengths of the telescope lenses.

Figure 2:
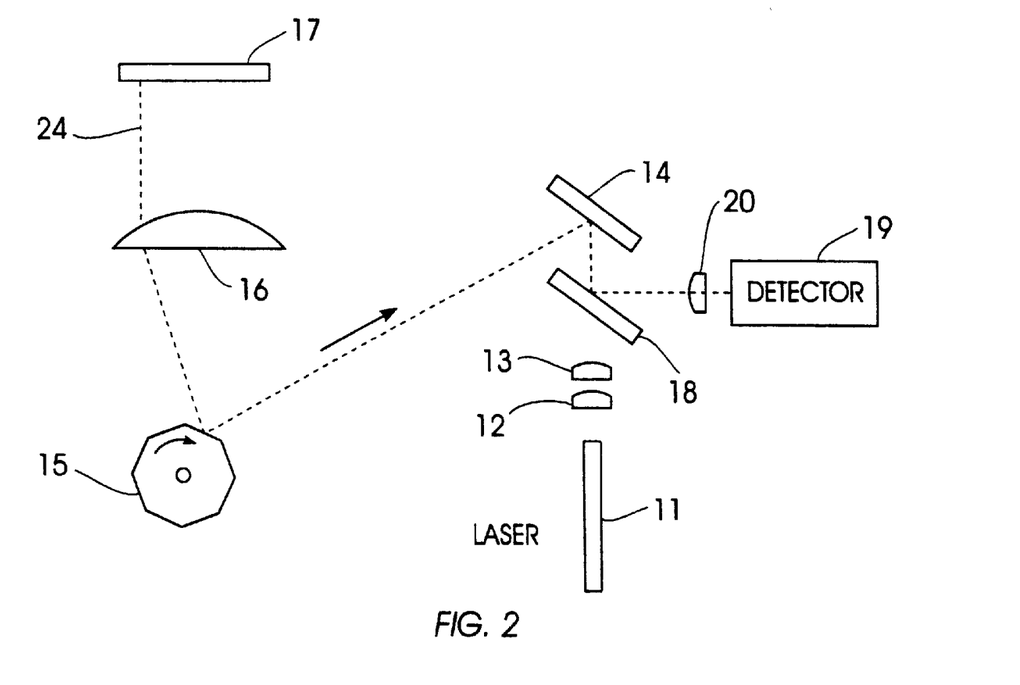
FIG. 2 shows the optical elements in the path for the reflected laser light from the surface being inspected.

FIG. 2 shows the optical elements in the path for the reflected beam 24 from the surface being inspected. The term "reflected beam" (or A/R beam) will be used to refer to all segments of the beam which are reflected from the object's surface as it follows the path to the detector. The surface of the object 17 reflects a portion of the incident beam to form a reflected beam 24 which follows a path back through the LIT, which is slightly offset from the path of the incident beam. (Note: The described embodiment inspects the planar surfaces of disks, but nonplanar surfaces could be inspected using the system if the nonplanarity is no more than a few degrees.) The reflected beam passes through the TLA 16 and is reflected by the scanner 15 back to mirror 14. Because the path of the reflected beam is offset from the incident beam, the reflected beam strikes capture mirror 18 which diverts the reflected beam through lens 20 which reduces the spot size of the beam striking detector 19. The detector is preferably a silicon detector which produces an analog signal which is a function of the amplitude of the reflected beam. The detector should have very low noise to preserve the sensitivity of the system. The LIT may function by detecting only relative shifts in the reflected beam as it scans across the surface and as the surface is translated under the beam, but it is advantageous to detect absolute reflectivity. The use of reflected light for inspection rather than scattered light allows a simplified approach and avoids the problems involved in trying to capture all of the scattered light. In addition, the use of reflected light allows detection of absorption changes and defects associated therewith.

Figure 3:
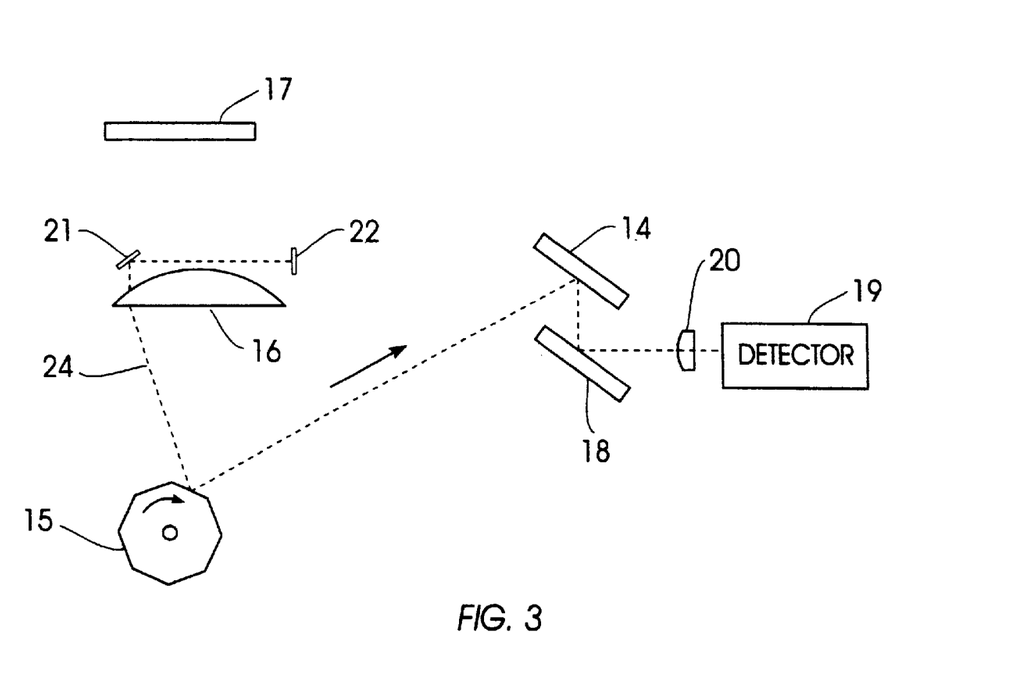
FIG. 3 shows the optical elements in the path for the reflected laser light from the calibration mirrors.

FIG. 3 shows an optional feature which provides a start of the scan signal and allows the detector to be calibrated to measure the absolute amplitude of the reflected beam. Measurement of the absolute reflectivity allows an additional class of defects and/or characteristics to be detected and/or measured, thus enhancing the capability of the tool. Calibration mirrors 21 and 22 are arranged so that an initial portion of the scan line falls on mirror 21, which reflects the beam to mirror 22 which reflects the beam back to mirror 21 and back into the TLA along the path for the reflected beam as described above. The length of the path of the beams going to and from the calibration mirrors is set equal to the length of the beam paths to and from the surface 17 to prevent spot size change. This arrangement creates a reference signal from the detector for each scan line which signals the start of scan, and is also known to correspond to the maximum possible magnitude of the reflected beam. Alternatively, a mirror could be positioned adjacent to the object being scanned to allow the beam to strike the mirror during the scan, but positioning the calibration mirrors away from the disk as shown in FIG. 3 is preferable since it reduces the number of fragile components near the mechanical moving parts. Having the maximum reference signal for comparison allows the amplitude of the reflected beam from the disk to be converted to an absolute measure of reflectivity. The signal from the calibration mirrors can be used as a start of scan without using it as an absolute amplitude reference. Once the beam strikes the calibration mirror 21, the reflected beam will slew to its maximum value. This transition from no reflected beam to the maximum forms a sharp edge in the analog output of the detector which can be used as the start-of-scan signal. A fixed delay can then be used to gauge the approximate time at which the scan line will be at the first data point on the disk. To avoid having false triggering from the other transitions in the signal at the edges of the disk, the circuitry which detects the start-of-scan signal should delay resetting until the scan line has cleared the last edge of the disk.

Figure 4:
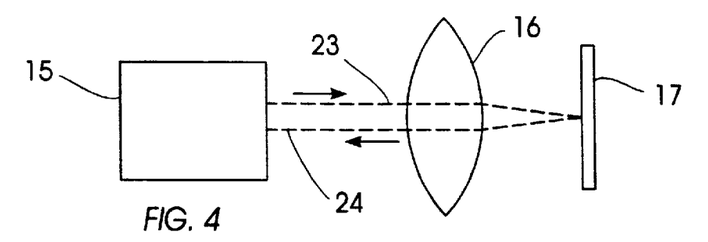
FIG. 4 shows the spatial relationship betweeen the incident beam and the reflected beam between the surface and polygon mirror.

FIG. 4 shows the preferred spatial relationship between the incident beam and the reflected beam between the surface 17 and polygon mirror 15. As previously noted, the reflected beam 24 is offset from the incident beam 23 to allow the reflected beam to be routed to the detector. This is achieved by causing the incident beam to strike the surface at a slight angle which causes the reflected beam to come off at a slight angle as shown in FIG. 4. As an example, an offset angle of a few degrees over a 125 mm path results in a beam offset on the order of 5–10 mm which easily allows the reflected beam to be routed to a mirror which is by-passed by the incident beam. The telecentric aspect of the TLA causes the reflected beam 24 to be essentially parallel to incident beam 23 after the reflected beam has passed through the TLA. The optical axis of the TLA should ideally split the angle formed by the incident and reflected beam at the surface to minimize the effects of coma and spherical aberration due to the beam separation.

Figure 5:
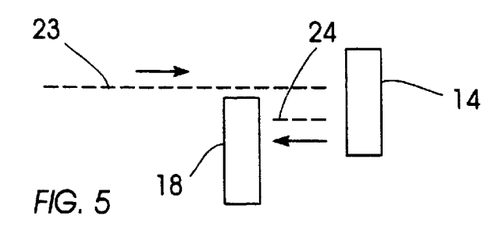
FIG. 5 shows the spatial relationship between the incident beam, the reflected beam, and the capture mirror.

FIG. 5 shows the spatial relationship between the incident beam and the reflected beam in relation to the capture mirror 18 and steering mirror 14. The incident beam 23 passes above the capture mirror 18 on its way to steering mirror 14. The reflected beam 24 is sufficiently offset to allow it to strike capture mirror 18 and to be routed to the detector. This arrangement is deemed superior to using a beam splitter with the signal losses associated therewith. It is feasible to allow the incident and reflected beam to be coincident until the reflected beam can be separated using an appropriate beam splitter, but the arrangement shown is deemed preferable. Beam splitters, which could be used if desired, include polarizing beam splitters, partially reflective beam splitters, or pellicle beam splitters.

Figures 6, 7:
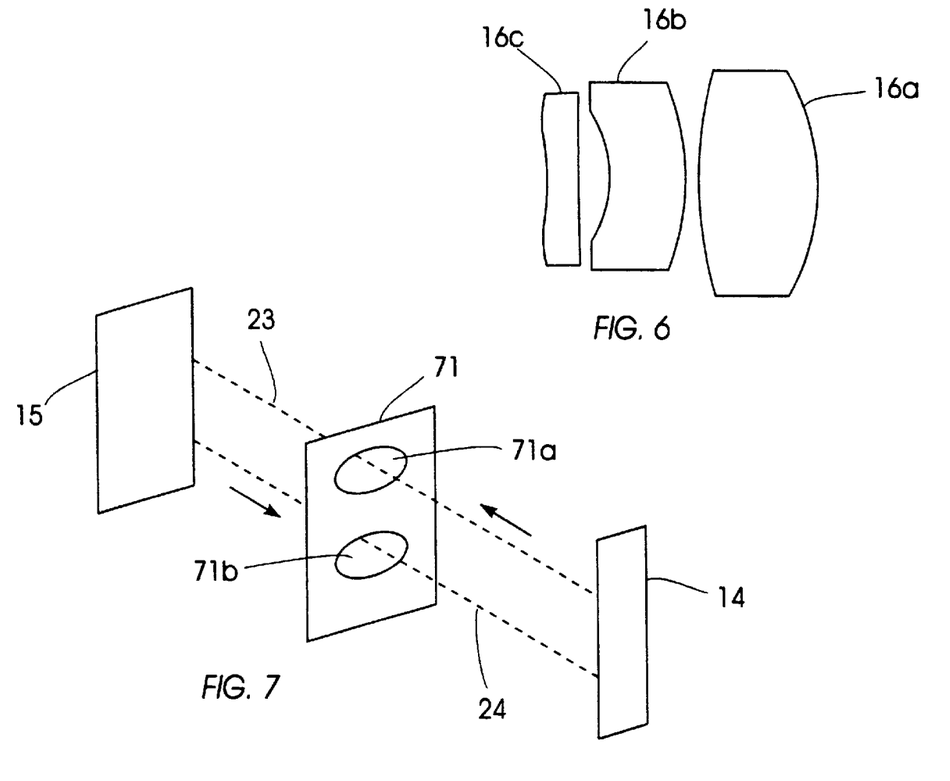
FIG. 6 shows a representative three-lens implementation of the telecentric lens assembly.
FIG. 7 shows an alignment aperture mask.

The TLA characteristics of the TLA 16 are tailored to the specifics of the application and particularly to the size of the surface being inspected. One standard size of disk for use in disk drives is 95 mm in diameter. For such a surface, the design of the TLA could be specified for the wavelength of the laser being used as a field of 105 mm, focal length of 125 mm, telecentricity of <0.5 degrees, and field curvature of <1.0 mm. FIG. 6 illustrates a three-element (elements 16a, 16b, 16c) spherical lens implementation which can be used to meet these requirements. Other implementations (including a single lens) may be used. An optical configuration which is capable of scanning 95 mm disks is also capable of being used to scan smaller disks. When smaller objects are being scanned, it may be desirable to increase the sampling rate in order to obtain the same number of pixels for the smaller object.

FIG. 7 shows an optional aperture mask 71, having apertures (holes) 71a and 71b, which is positioned between scanner 15 and mirror 14 (see FIG. 2) so that the incident beam 23 passes through aperture 71a and reflected beam 24 passes through aperture 71b. The aperture mask is made from opaque material and the apertures are sized to limit the cone of scattered light that passes through. Limiting the cone of the reflected beam is more important than for the incident beam. The reflected beam cone size should be limited to removing some of the near-forward scattered light to improve the sensitivity of the detector to reflected light. The size of the aperture for the reflected light should be selected empirically for the particular application by scanning a surface feature known to produce near-forward scattered light, e.g., laser texture bumps on disks. The aperture should not be overly restrictive, however, since variation in the polygon faces, etc. will cause some tolerances to exist in the reflected beam. Using an aperture of approximately six times the diameter of the beam in the arrangement shown was found to result in a superior detection capability for the laser texture zone. The masking of the near-forward scattered light can be performed at various points in the path of the reflected beam, e.g., at the detector, but the position of the aperture mask as shown has the additional benefit of providing an aid for coarse alignment of the beams which should be positioned in the center of the apertures. Optionally, a removable translucent member may be placed over the apertures to enhance the visibility of the beam position during alignment. Various other alignment features and aids may be incorporated into the design of the LIT. For use in a manufacturing environment, it is important that alignment be easy to obtain and to maintain. In a two-channel implementation, the disk must be centered between the two TLAs and be perpendicular to the horizontal axis of the system. The position of the disk holder with respect to the optics board is adjusted, then the distance position along the mounting rail of the TLAs is adjusted. Preferably, several of the components in the optical path will have X–Y adjustments, but it is not required that they all have adjustments. The lenses 12, 13 comprising the telescope are likewise mounted on rails to allow the distance between them to be adjusted to control spot size. At least one of the lenses in the telescope should preferably have a fine position adjustment. The apertures in the aperture mask may also be used during the finer alignment process by positioning target plugs in the apertures which have small diameter alignment holes, e.g., 1 mm in diameter, positioned at the central point where the beams are properly aligned. One or more similar targets with alignment holes may be used in the path from the laser to the steering mirror. If the laser and the telescope lenses are mounted on an optical rail, one or more targets with alignment holes can be placed on the rail and moved along the rail if desired to aid in the X–Y alignment of the laser. The approximate alignment of the beams can be observed visually since misalignment will reduce the intensity of the beam passing through the small holes. After coarse alignment has been achieved, the amplitude of the beam as measured by the detector 19 provides a precise aid for alignment of the entire path. The X–Y adjustments of the laser, the steering mirror, etc. are used to achieve maximum amplitude of the output signal at the detector from a reference disk having at least a portion which is used as a defect-free standard. The TLA 16 determines the spot focusing and telecentricity of the beam. Telecentricity is determined by the spacing of the TLA to the polygon 15, and is set using the scan lens micrometer which translates the TLA along the axis between the polygon and the disk. The input beam collimation of the incident beam entering the TLA is set by adjusting the spacing between lenses 12 and 13 of the telescope. The circularity of the return beam after reflection from the polygon is a function of the telecentricity and can be used during alignment. Spot size should be reasonably constant through a scan so spot size should be measured across the scan field using a spot size measuring instrument positioned in the scan plane at multiple scan positions. If the deviation in spot size is too large, additional alignment is needed.

Polygon Synchronization

Figure 8:
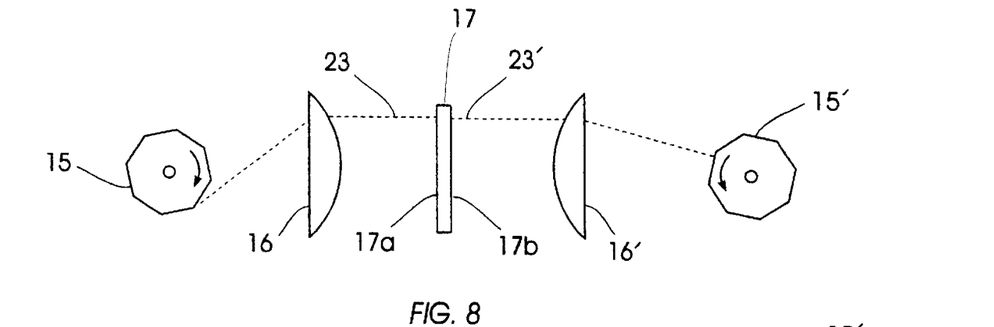
FIG. 8 shows the polygon scanner orientations in a two-channel embodiment.
Figure 9:
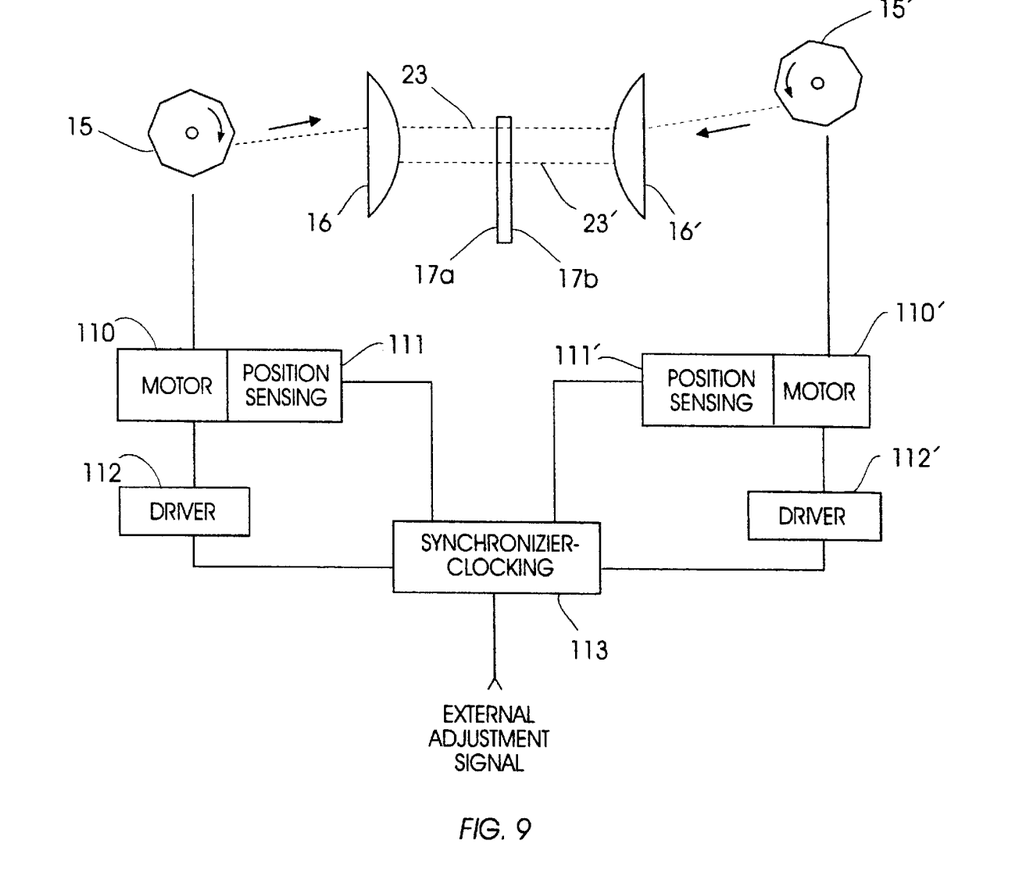
FIG. 9 illustrates a control system for synchronizing and offsetting the rotation of the polygon scanners.

In a two-channel implementation of the invention, i.e., a LIT which inspects both planar surfaces of a disk simultaneously, there are several options on how the A and B beams can be spaced and coordinated with each other. Interference between the channels will occur when the beams pass through the central hole in the disk unless steps are taken to prevent it. A similar problem might arise if the LIT is being used to inspect any object having holes and/or transparent portions. The polygons can be arranged to rotate in a common direction which will result in the scan on each side of the disk proceeding in opposite directions and crossing in the center of the scan area. When the beams cross, there will be crosstalk as the beam from the opposite channel reaches the detectors. One arrangement to minimize interference has the B beam vertically displaced from the A beam, but this causes difficulties in building the tool and coordinating the data. A preferred arrangement is shown in FIG. 8. FIG. 8 shows the polygon scanner orientations in a two-channel embodiment where the polygons 15, 15' are coplanar, but spin in opposite directions which results in the two beams 23, 23' maintaining a fixed relationship to each other as they scan. In a preferred embodiment, the rotational position of the two polygon mirror scanners is synchronized. This will allow the beam from the A side optics to be transmitted to the B side where it is "descanned" by the polygon mirror. FIG. 9 illustrates a control system for synchronization and offset of the polygons. Beams 23, 23' are shown passing through the hole in the disk. The beams are only shown up to the TLAs 16, 16' but each will, of course, pass through the transparent lenses and be reflected from the polygon facet. The separation between the beams is shown greatly exaggerated so that the offset is clearly visible. The polygons are rotated by DC motors 110, 110' which have integral position sensing units 111, 111' which can provide index pulses as well as a binary value indicating the angular position of the motor. The positional signals are fed back into the synchronizer/clocking unit 113. This provides signals to the motor drivers 112, 112' which control the speed and phase of the motors. Using the position feedback and an external input, the synchronizer/clocking unit retards or advances the phase of one of the motors (e.g., motor 110') to allow the magnitude of the offset between the two motors to be controlled while maintaining the same rotational speed. The external input signal can be as simple as a pulse generated by an operator pressing a switch which causes the phase to advance a few microseconds for each pulse. One convenient way to set the offset is to adjust for zero motion of the descanned signal. An operator could do this by observing an oscilloscope trace of the output of the detector and bumping the phase switch until the signal change with time is essentially zero.

Elimination of Interference Fringes in Glass Substrate Testing

The present invention uses the previously-described LIT with minor modifications. The resulting system, unlike the LIT that uses reflective light, uses light transmitted through the substrate being inspected. The system does not operate on both the A side and B side simultaneously. Instead, the light generation and direction system of one side (A side) is used with the light reflection and detection system of the other side (B side). The beam follows a first optical path from the laser to the first planar surface of the disk substrate and a second optical path, after transmission through the substrate, from the second planar surface of the disk substrate to the light detector.

Figure 10:
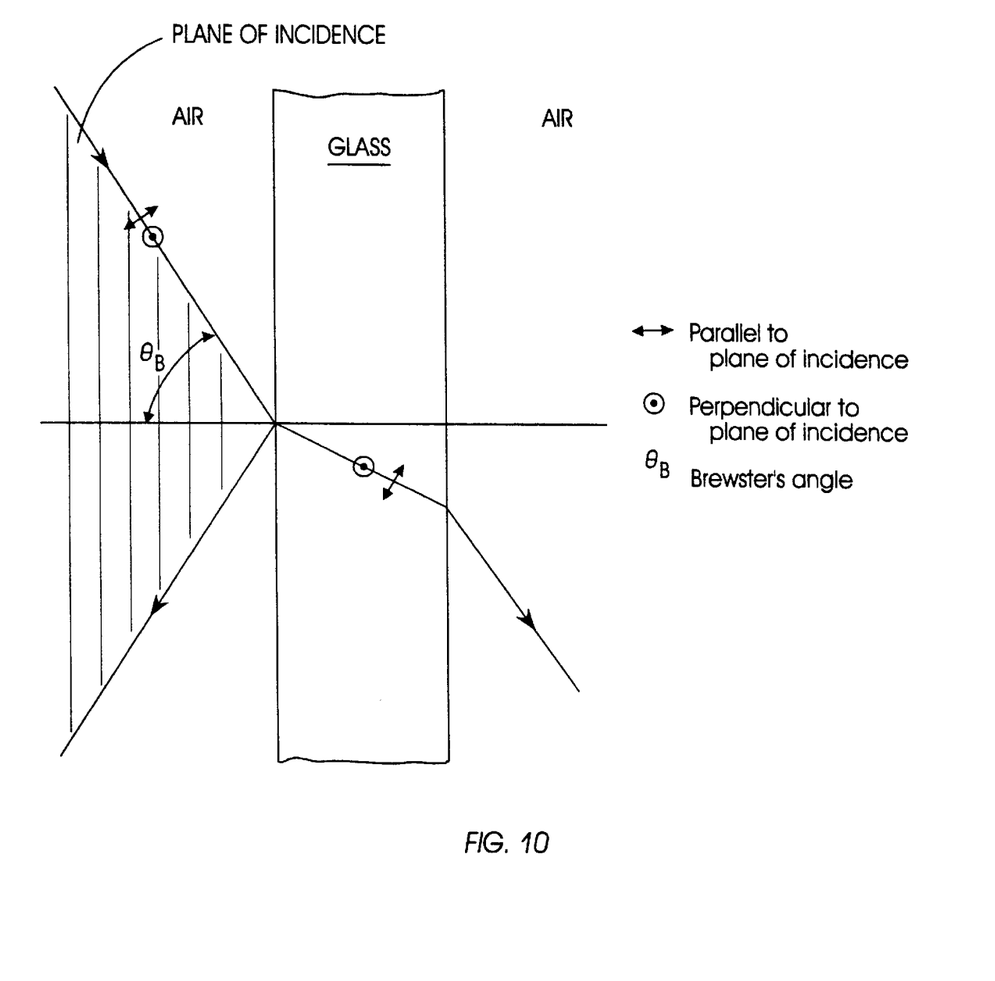
FIG. 10 shows the Brewster angle geometry for inspection of glass disk substrates.

It is well known that at Brewster's angle of incidence, all light polarized parallel to the plane of incidence is transmitted. The plane of incidence is defined as the plane formed by the line of the incident light and a line perpendicular to the surface being inspected. For use of the LIT with glass or other types of light-transmissive substrates, this principle is applied as shown in FIG. 10. For incident light of arbitrary polarization, light is considered as being split into two components, one being parallel to and the other perpendicular to the plane of incidence. The component parallel to the plane of incidence is 100% transmitted, while the component perpendicular to the plane of incidence is partially transmitted and partially reflected. Thus, if only light polarized parallel to the plane of incidence is used, all the light is transmitted and there is no surface reflection at either the first or second surfaces of the disk substrate. Consequently, no interference fringes are produced.

Preferred Implementation for Glass Substrates

Figure 11:
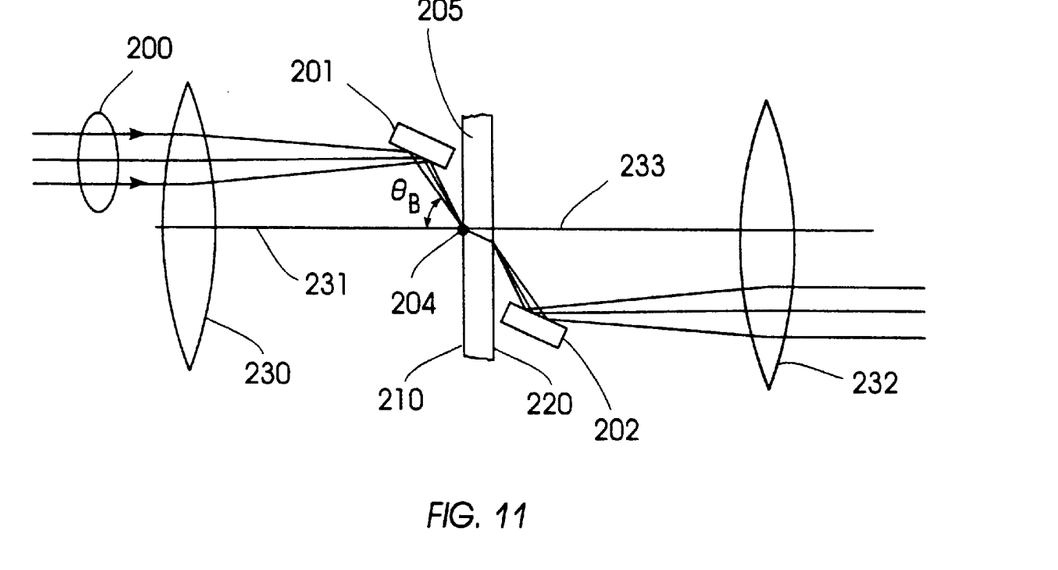
FIG. 11 shows a side view of the preferred embodiment.
Figure 12:
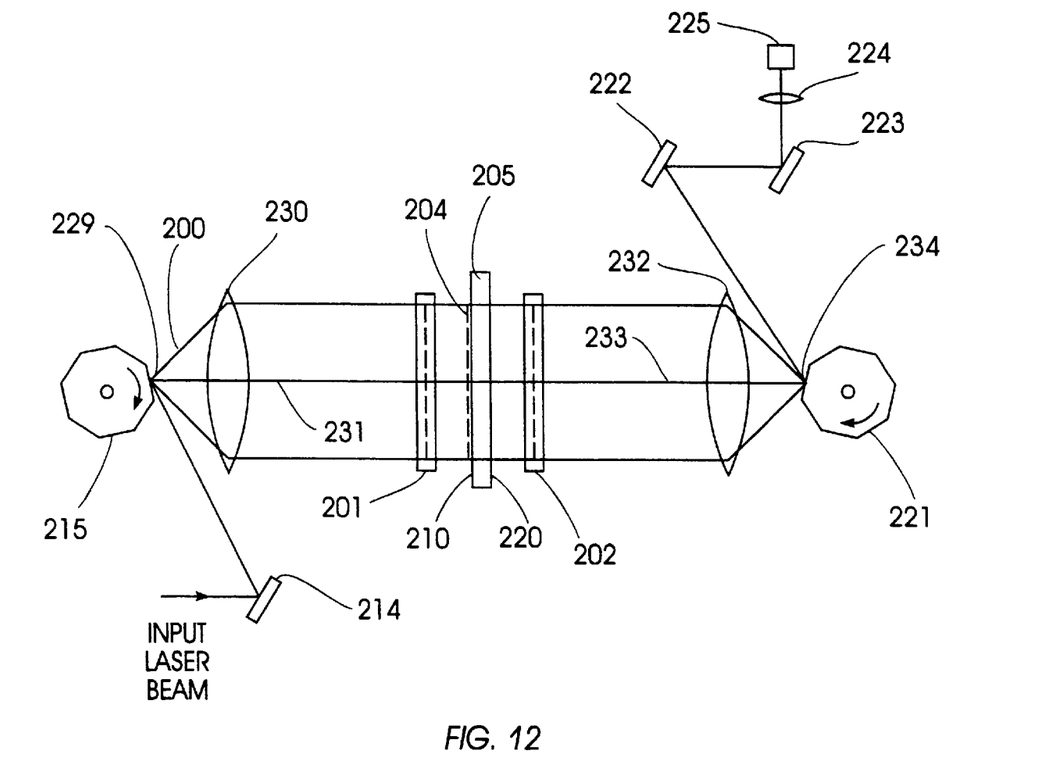
FIG. 12 shows the top view of the preferred embodiment.

A preferred implementation of the invention for glass substrates is shown in FIGS. 11–12. FIG. 11 is a side view wherein the scan line 204 on the first planar surface 210 of the disk substrate 205 is shown as being perpendicular to the paper. This scan line 204 is represented as dashed line 204 on surface 210 in FIG. 12, which is a top view. The incident laser beam 200 enters through a first telecentric lens assembly 230 having an optical axis 231. The first telecentric lens assembly 230 receives the light beam from the rotating polygon mirror scanner 215 along paths that are not parallel to optical axis 231 and outputs the beam along paths that are generally parallel to optical axis 231. The beam that is input to telecentric lens assembly 230 emanates from its focal point 229, which is located at the point where the beam has been reflected by rotating polygon mirror scanner 215.

A pair of fixed mirrors 201, 202 are used. The first fixed mirror 201 directs the beam from first telecentric lens assembly 230 so that it strikes the first planar surface 210 of glass disk 205 at Brewster's angle. The beam is totally transmitted at the first surface 210 through the substrate 205 and exits the second planar surface 220. After emerging from the second disk surface 220, the beam strikes the second fixed mirror 202 which redirects the beam into a second telecentric lens assembly 232 having an optical axis 233. The beam passes through the second telecentric lens assembly 232 in the reverse direction to the direction it passed through the first telecentric lens assembly 230. Thus second telecentric lens assembly 232 receives the beam from second fixed mirror 202 along paths that are generally parallel to its optical axis 233 and directs the beam along paths nonparallel to its optical axis toward its focal point 234. This focal point 234 of telecentric lens assembly 232 is located at the point where the beam strikes the second rotating polygon mirror scanner 221. Since the previously-described LIT uses two symmetrical scanning systems to inspect both sides of the disk substrate 205, the second mirror 202 redirects the emerging beam into the second scanning system where it is descanned by the second polygon mirror and passes to the photodetector 225. Note that a height adjustment may be required to ensure that the descanned beam is at the correct height for detection by the photodetector. This can be easily accomplished by changing the relative heights of the two sides of the system.

Figure 13:
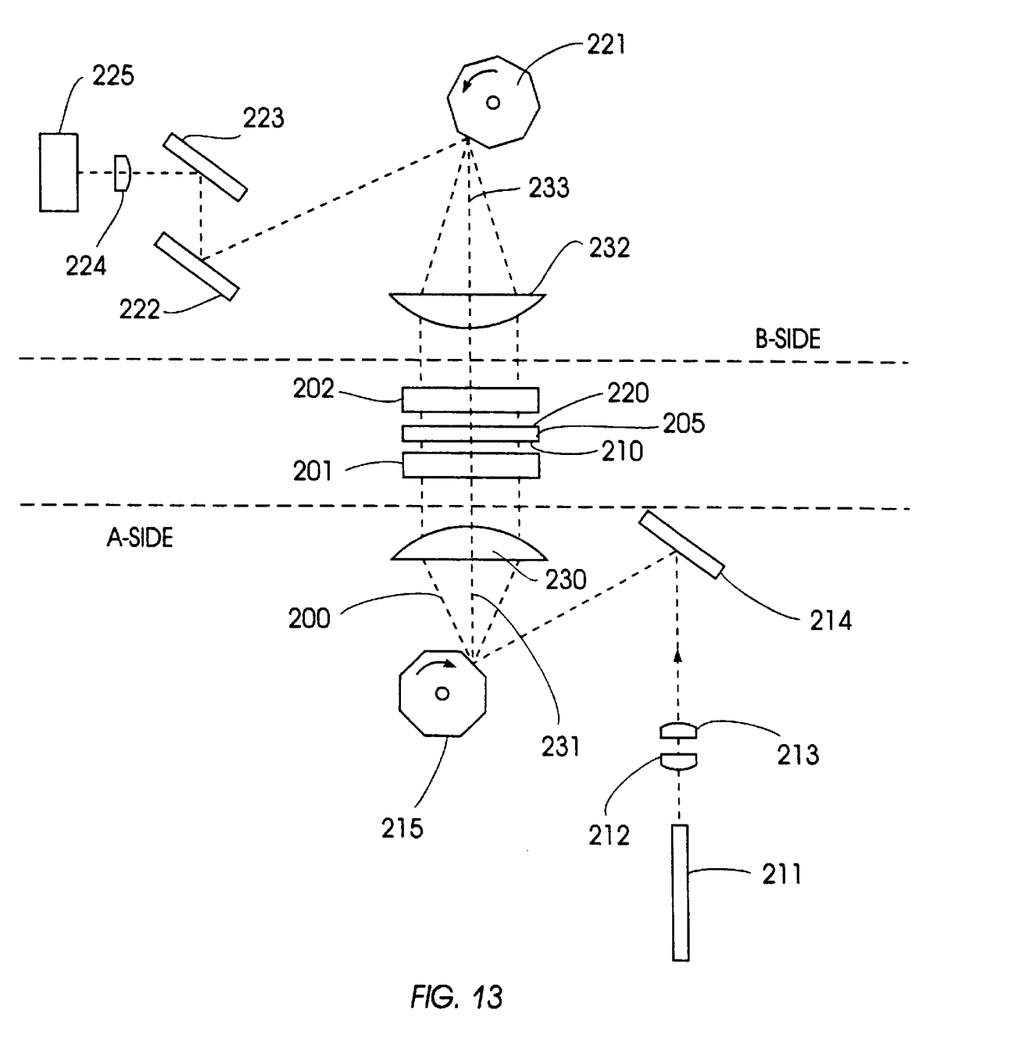
FIG. 13 shows a top view of the optical layout of the system for inspection of glass disk substrates that uses the preferred embodiment of two telecentric lens assemblies and two synchronized rotating polygon mirror scanners.

A top view of the layout of the system for inspection of the glass substrates is shown in FIG. 13. The scanning beam is produced by the lower portion of the optical system (normally the A side reflective measurement system of the previously-described LIT). The beam passes through the glass disk substrate 205 and is then picked up and descanned by the upper portion of the optical system (normally the B side reflective measurement system of the LIT). By using polarized light incident at Brewster's angle, all of the measurement light is transmitted through the glass disk substrate 205 and no interference fringes are formed by the two parallel planar disk surfaces 210, 220. A polarized laser 211 is used as the light source. A suitable laser is a He-Ne laser, such as Model 1107P from Uniphase. Alternatively, a conventional nonpolarizing laser can be used together with conventional polarizing optical elements. The light passes from laser 211 through a telescope formed of lens elements 212 and 213 for beam size adjustment. It is then reflected from a fold mirror 214 and directed to the first rotating polygon mirror scanner 215. The scanner 215 produces a linear scanning beam that is focused by a telecentric lens assembly 230 onto the first planar surface 210 of the glass disk substrate 205 to be inspected. As the polygon mirror scanner 215 rotates, the beam is scanned across the input to telecentric lens assembly 230. The fold mirror 201 directs the beam onto the first planar surface 210 of the disk substrate 205 at Brewster's angle, so that during scanning the beam strikes the planar surface 210 of disk substrate 205 along scan line 204. The beam is transmitted through substrate 205 and is then redirected by fold mirror 202 toward the second telecentric lens assembly 232. The beam is then descanned by second polygon mirror scanner 221 and subsequently directed onto a detector 225 after reflection from fold mirrors 222 and 223 and focusing lens 224.

In the present invention, the entire glass disk substrate is inspected (i.e., both surfaces 210, 220 and the bulk material between the two surfaces). Thus, a measure of total disk substrate quality includes the defects from both surfaces. For example, if a single-sided acceptable quality level of 100 pixel defects is allowed, then the criteria for glass substrate inspection would be 200 pixel defects, which includes defects on both surfaces. Because the typical glass disk substrates used for magnetic recording disks are of a very high purity, defects within the bulk material are negligible and do not affect the signal received at detector 225.

As can be understood from FIGS. 11–13 and the previously-described LIT, the present invention allows light-transmissive disk substrates to be inspected for surface defects with only minor modifications to the LIT. The only elements required to be added to the LIT are fold mirror 201, which directs the light to strike the planar surface 210 at Brewster's angle, fold mirror 202, which redirects the transmitted light, and means for generating polarized light so that only light polarized in the plane of incidence strikes the first surface 210 of substrate 205.

The invention has been shown and described in the preferred embodiment with the use of a fixed mirror 201 that directs light to the planar surface of the substrate at Brewster's angle, with this mirror being located between the telecentric lens assembly and the substrate. However, by suitable mechanical arrangement of the system the telecentric lens assembly can be located relative to the substrate holder so that the output of the telecentric lens assembly is oriented directly to the substrate surface at Brewster's angle, without the need for mirrors or other optical elements, or with a mirror located between the scanner and the telecentric lens assembly.

In the preferred embodiment the invention is incorporated into the LIT and thus uses the second telecentric lens assembly and polygon mirror scanner to direct the transmitted light to the detector. However, the invention may also be used with a detector located near the second planar surface of the disk substrate for directly receiving light transmitted through the substrate.

Figure 14:
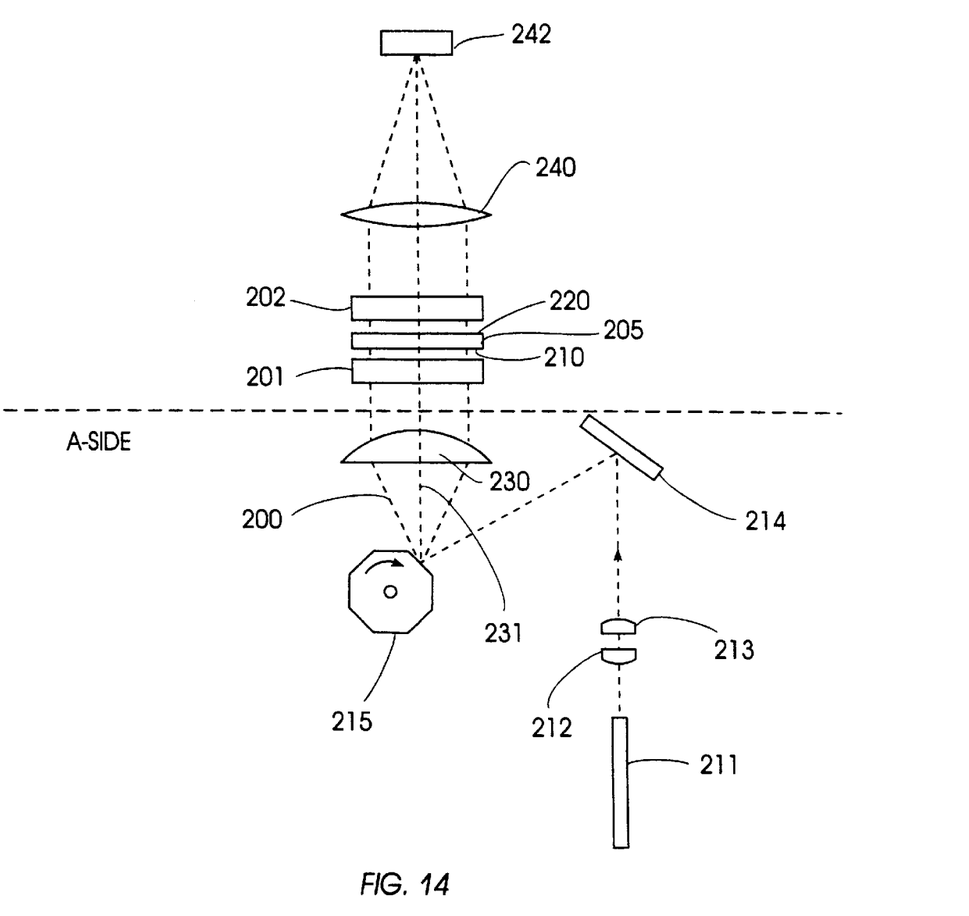
FIG. 14 shows a top view of the optical layout of the system for inspection of glass disk substrates that uses an alternative embodiment with a single telecentric lens assembly and rotating polygon mirror scanner on one side of the object and a collecting lens and detector on the other side of the object.

In an alternative embodiment, as shown in FIG. 14, a collection lens 240, which need not be a telecentric lens assembly, is located on the other side of the disk substrate 205 in the second optical path beyond the second fixed mirror 202. The collection lens 240 focuses the light to detector 242. The spot focused by the collection lens 240 will not be as small as the spot focused by a telecentric lens and the spot will experience a small amount of motion about the focal point, but the detector 242 is large enough to accomodate these minor variations.

While the present invention has been particularly shown and described with reference to the preferred embodiments, it will be understood by those skilled in the art that various changes in form and detail may be made without departing from the spirit, scope, and teaching of the invention. Accordingly, the disclosed invention is to be considered merely as illustrative and limited in scope only as specified in the appended claims.

What is claimed is:

1. An apparatus for detecting defects in a light-transmissive object having first and second planar surfaces, the apparatus comprising:

a laser for generating a laser beam, the laser beam being directed along a first optical path to the first planar surface of the object to strike the first planar surface of the object at Brewster's angle and being polarized in a plane formed by the laser beam and a line perpendicular to said first planar surface;

a first movable mirror located in the first optical path for scanning the beam across a portion of said first planar surface;

a first telecentric lens assembly located in the first optical path between the first movable mirror and the object for causing the beam to strike said first planar surface at substantially the same angle during scanning of the beam across said first planar surface; and a light detector for receiving light transmitted through said first and second planar surfaces of the light-transmissive object along a second optical path from said second planar surface, the light detector producing a signal proportional to the intensity of the received light.

2. The apparatus of claim 1 further comprising means located in the first optical path for directing the beam to strike said first planar surface at Brewster's angle during scanning of the beam across said first planar surface.

3. The apparatus of claim 2 wherein the Brewster's angle beam directing means is a fixed mirror located between the telecentric lens assembly and the object.

4. The apparatus of claim 1 wherein the first movable mirror is a rotating mirror.

5. The apparatus of claim 4 wherein the rotating mirror is a polygon mirror.

6. The apparatus of claim 1 further comprising a movable support for the object which moves the object through the beam, whereby different portions of said first planar surface are scanned.

7. The apparatus of claim 1 wherein the laser is a polarizing laser.

8. The apparatus of claim 1 wherein the laser is a nonpolarizing laser and further comprising a polarizer located in the first optical path.

9. The apparatus of claim 1 wherein the signal from the detector is an analog signal, and further comprising:
   means for sampling and digitizing the analog signal from the detector to generate pixel data; and
   means for analyzing the rate of change of the pixel data to detect defects or features associated with rates of change exceeding a selected threshold.

10. The apparatus of claim 1 wherein the signal from the detector is an analog signal, and further comprising:
    at least one mirror arranged to reflect a portion of the beam to generate a reference signal;
    means for sampling and digitizing the analog signal from the detector to generate pixel data; and
    means for determining the transmissivity of the object by comparing the pixel data with the reference signal.

11. The apparatus of claim 1 further comprising
    a second movable mirror located in the second optical path between said second planar surface and the detector; and
    a second telecentric lens assembly located in the second optical path between said second planar surface and the second movable mirror.

12. The apparatus of claim 11 wherein the first and second movable mirrors are rotatable polygon mirrors that lie in a common plane and the first rotating mirror rotates in an opposite direction from the second rotating mirror, and further comprising means for synchronizing the rotation of the first and second rotating mirrors.

13. The apparatus of claim 1 further comprising a collection lens located in the second optical path between said second surface and the detector for focusing light transmitted through the object to the detector.

14. An apparatus for detecting defects in a glass disk substrate having parallel first and second planar surfaces, the apparatus comprising:
    a laser for generating a laser beam, the laser beam being directed along a first optical path to the first planar surface of the disk substrate and being polarized in a plane formed by the laser beam and a line perpendicular to said first planar surface;
    a first telecentric lens assembly having an optical axis and being located in the first optical path for receiving the beam nonparallel to the optical axis and outputting the beam generally parallel to the optical axis;
    a first rotating polygon mirror scanner located in the first optical path between the laser and the first telecentric lens assembly for scanning the beam across the first telecentric lens assembly;
    a first fixed mirror located in the first optical path between the first telecentric lens assembly and the first planar surface for directing the beam from the first telecentric lens assembly to strike said first planar surface at Brewster's angle as the beam is scanned across said first planar surface;
    a movable support for the disk substrate for moving the disk substrate in a plane parallel to said first planar surface, whereby after the beam is scanned across a first portion of said first planar surface the disk substrate is moved by the support for subsequent scanning of a second portion of said first planar surface;
    a light detector for receiving the beam transmitted through said first and second planar surfaces of the disk substrate along a second optical path from said second planar surface, the light detector producing a signal proportional to the intensity of the received light;
    a second telecentric lens assembly having an optical axis and being located in the second optical path between said second planar surface and the detector for receiving the beam generally parallel to the optical axis and outputting the beam nonparallel to the optical axis;
    a second fixed mirror located in the second optical path between said second planar surface and the second telecentric lens assembly for receiving the beam from said second planar surface and redirecting the beam to be generally parallel to the optical axis of the second telecentric lens assembly;
    a second rotating polygon mirror scanner located in the second optical path between the second telecentric lens assembly and the detector for directing the beam from the second telecentric lens assembly to the detector, wherein the axes of rotation of the first and second rotating polygon mirror scanners lie in a common plane and the first rotating polygon mirror scanner rotates in an opposite direction from the second rotating polygon mirror scanner; and
    means for synchronizing the rotation of the first and second rotating polygon mirror scanners.

15. The apparatus of claim 14 wherein the laser is a polarizing laser.

16. The apparatus of claim 14 wherein the laser is a nonpolarizing laser and further comprising a polarizer located in the first optical path.

17. The apparatus of claim 14 wherein the signal from the detector is an analog signal, and further comprising:
    means for sampling and digitizing the analog signal from the detector to generate pixel data; and
    means for analyzing the rate of change of the pixel data to detect defects or features associated with rates of change exceeding a selected threshold.

18. The apparatus of claim 14 wherein the signal from the detector is an analog signal, and further comprising:
    at least one mirror arranged to reflect a portion of the beam to generate a reference signal;
    means for sampling and digitizing the analog signal from the detector to generate pixel data; and
    means for determining the transmissivity of the disk substrate by comparing the pixel data with the reference signal.

* * * * *